US012369618B2

United States Patent
Tucker et al.

(10) Patent No.: US 12,369,618 B2
(45) Date of Patent: *Jul. 29, 2025

(54) ELECTRONIC VAPING DEVICE INCLUDING TRANSFER PAD WITH ORIENTED FIBERS

(71) Applicant: Altria Client Services LLC, Richmond, VA (US)

(72) Inventors: Christopher S. Tucker, Midlothian, VA (US); William J. Crowe, Richmond, VA (US); Geoffrey Brandon Jordan, Midlothian, VA (US); Bipin R. Patil, Richmond, VA (US); Jarrett Keen, Richmond, VA (US); Michael Roberts, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 135 days.

This patent is subject to a terminal disclaimer.

(21) Appl. No.: 16/992,810

(22) Filed: Aug. 13, 2020

(65) Prior Publication Data
US 2021/0022397 A1    Jan. 28, 2021

Related U.S. Application Data

(63) Continuation of application No. 15/729,895, filed on Oct. 11, 2017, now Pat. No. 10,772,356.

(51) Int. Cl.
*A24F 13/00* (2006.01)
*A24B 15/167* (2020.01)
(Continued)

(52) U.S. Cl.
CPC .......... *A24B 15/283* (2013.01); *A24B 15/167* (2016.11); *A24F 40/42* (2020.01);
(Continued)

(58) Field of Classification Search
CPC ....................................................... A24F 47/00
(Continued)

(56) References Cited

U.S. PATENT DOCUMENTS

| 4,083,372 A | 4/1978 | Boden |
| 5,034,721 A | 7/1991 | Benedictus |

(Continued)

FOREIGN PATENT DOCUMENTS

| CN | 202489175 U | 10/2012 |
| CN | 203446525 U | 2/2014 |

(Continued)

OTHER PUBLICATIONS

U.S. Notice of Allowance dated Oct. 27, 2020 for corresponding U.S. Appl. No. 15/931,999.

(Continued)

*Primary Examiner* — Phuong K Dinh
(74) *Attorney, Agent, or Firm* — Harness, Dickey & Pierce, P.L.C.

(57) ABSTRACT

A cartridge for an electronic vaping device includes an outer housing extending in a longitudinal direction and a reservoir configured to contain a pre-vapor formulation. The reservoir is in the outer housing. The reservoir has a first reservoir end and a second reservoir end. The cartridge also includes a seal at the first reservoir end, a transfer pad at the second reservoir end, and a wick in contact with the transfer pad. The transfer pad includes a plurality of fibers. Each of the plurality of fibers is substantially parallel to the longitudinal direction.

23 Claims, 7 Drawing Sheets

(51) Int. Cl.
*A24B 15/28* (2006.01)
*A24F 40/42* (2020.01)
*A24F 40/70* (2020.01)
*A61L 9/03* (2006.01)
*B65B 3/04* (2006.01)
*H05B 3/14* (2006.01)
*A24D 3/06* (2006.01)
*A24F 40/10* (2020.01)
*H05B 3/06* (2006.01)
*H05B 3/16* (2006.01)

(52) U.S. Cl.
CPC .............. *A24F 40/70* (2020.01); *A61L 9/037* (2013.01); *B65B 3/04* (2013.01); *H05B 3/141* (2013.01); *A24D 3/063* (2013.01); *A24F 40/10* (2020.01); *A61L 2209/111* (2013.01); *A61L 2209/12* (2013.01); *H05B 3/06* (2013.01); *H05B 3/16* (2013.01); *H05B 2203/021* (2013.01)

(58) Field of Classification Search
USPC .................................................. 131/328–329
See application file for complete search history.

(56) References Cited

U.S. PATENT DOCUMENTS

| | | | |
|---|---|---|---|
| 5,388,594 A | 2/1995 | Counts et al. |
| 5,665,262 A | 9/1997 | Hajaligol et al. |
| 5,750,964 A | 5/1998 | Counts et al. |
| 6,155,268 A | 12/2000 | Takeuchi |
| 6,603,924 B2 | 8/2003 | Brown et al. |
| 6,719,405 B1 | 4/2004 | Powers |
| 8,191,555 B2 | 6/2012 | Herbrich et al. |
| 8,375,957 B2 | 2/2013 | Hon |
| 8,393,331 B2 | 3/2013 | Hon |
| D688,415 S | 8/2013 | Kim |
| 8,499,766 B1 | 8/2013 | Newton |
| 8,528,569 B1 | 9/2013 | Newton |
| D693,053 S | 11/2013 | Chen |
| D695,450 S | 12/2013 | Benassayag et al. |
| 8,746,240 B2 | 6/2014 | Terry et al. |
| 8,757,147 B2 | 6/2014 | Terry et al. |
| 8,794,231 B2 | 8/2014 | Thorens et al. |
| 8,833,364 B2 | 9/2014 | Buchberger |
| 8,851,068 B2 | 10/2014 | Cohen et al. |
| D720,095 S | 12/2014 | Alima |
| D720,496 S | 12/2014 | Alima |
| D720,881 S | 1/2015 | Liu |
| D724,782 S | 3/2015 | Wu |
| D728,155 S | 4/2015 | Liu |
| D728,156 S | 4/2015 | Wu |
| D729,441 S | 5/2015 | Hua |
| 9,055,617 B2 | 6/2015 | Thorens et al. |
| 9,072,321 B2 | 7/2015 | Liu |
| 9,095,175 B2 | 8/2015 | Terry et al. |
| 9,101,729 B2 | 8/2015 | Liu |
| 9,210,738 B2 | 12/2015 | Ward et al. |
| 9,210,739 B2 | 12/2015 | Chabach et al. |
| D748,852 S | 2/2016 | Wu |
| D749,260 S | 2/2016 | Wu |
| D751,249 S | 3/2016 | Chen |
| 9,271,525 B2 | 3/2016 | Liu |
| 9,282,772 B2 | 3/2016 | Tucker et al. |
| 9,289,014 B2 | 3/2016 | Tucker et al. |
| D758,649 S | 6/2016 | Liu |
| D764,703 S | 8/2016 | Liu |
| D765,307 S | 8/2016 | Liu |
| 9,420,829 B2 | 8/2016 | Thorens et al. |
| 9,427,711 B2 | 8/2016 | Terry et al. |
| D765,907 S | 9/2016 | Liu |
| 9,439,455 B2 | 9/2016 | Alarcon et al. |
| D774,247 S | 12/2016 | Chen |
| 9,510,623 B2 | 12/2016 | Tucker et al. |
| D778,492 S | 2/2017 | Liu |
| D778,493 S | 2/2017 | Scott |
| D780,372 S | 2/2017 | Liu |
| D784,610 S | 4/2017 | Bosch |
| D785,859 S | 5/2017 | Pang |
| 9,949,510 B2 | 4/2018 | Liu |
| D827,195 S | 8/2018 | Chen |
| D833,064 S | 11/2018 | Verleur et al. |
| D834,246 S | 11/2018 | Qiu |
| D835,337 S | 12/2018 | Beer et al. |
| D835,574 S | 12/2018 | Trongone |
| 10,226,076 B2 | 3/2019 | Althorpe et al. |
| 10,440,997 B2 | 10/2019 | Borkovec et al. |
| 10,506,827 B2 | 12/2019 | Guo et al. |
| 10,687,557 B2 | 6/2020 | Tucker et al. |
| 10,772,356 B2 * | 9/2020 | Tucker ................. A24B 15/167 |
| 10,932,496 B2 | 3/2021 | Tucker et al. |
| 11,930,843 B2 | 3/2024 | Tasselli et al. |
| 2006/0231641 A1 | 10/2006 | Uchiyama et al. |
| 2010/0293979 A1 | 11/2010 | Shei et al. |
| 2011/0126848 A1 | 6/2011 | Zuber et al. |
| 2011/0155153 A1 | 6/2011 | Thorens et al. |
| 2013/0019887 A1 | 1/2013 | Liu |
| 2013/0192623 A1 | 8/2013 | Tucker et al. |
| 2013/0213419 A1 | 8/2013 | Tucker et al. |
| 2013/0255675 A1 | 10/2013 | Liu |
| 2013/0306064 A1 | 11/2013 | Thorens et al. |
| 2013/0306065 A1 | 11/2013 | Thorens et al. |
| 2014/0048086 A1 | 2/2014 | Zhanghua |
| 2014/0053856 A1 | 2/2014 | Liu |
| 2014/0261487 A1 | 9/2014 | Chapman et al. |
| 2014/0270729 A1 | 9/2014 | DePiano et al. |
| 2014/0283855 A1 | 9/2014 | Hawes et al. |
| 2014/0283859 A1 | 9/2014 | Minskoff et al. |
| 2014/0345635 A1 | 11/2014 | Rabinowitz et al. |
| 2015/0020823 A1 | 1/2015 | Lipowicz et al. |
| 2015/0027470 A1 | 1/2015 | Kane et al. |
| 2015/0083147 A1 | 3/2015 | Schiff et al. |
| 2015/0101625 A1 | 4/2015 | Newton et al. |
| 2015/0128973 A1 | 5/2015 | Li et al. |
| 2015/0144145 A1 | 5/2015 | Chang et al. |
| 2015/0181930 A1 | 7/2015 | Liu |
| 2015/0181944 A1 | 7/2015 | Li et al. |
| 2015/0216233 A1 | 8/2015 | Sears et al. |
| 2015/0216234 A1 | 8/2015 | Chung |
| 2015/0216236 A1 | 8/2015 | Bless et al. |
| 2015/0245654 A1 | 9/2015 | Memari et al. |
| 2015/0245658 A1 | 9/2015 | Worm et al. |
| 2015/0245669 A1 | 9/2015 | Cadieux et al. |
| 2015/0272217 A1 | 10/2015 | Chen |
| 2015/0305408 A1 | 10/2015 | Liu |
| 2015/0305410 A1 | 10/2015 | Liu |
| 2015/0313275 A1 | 11/2015 | Anderson et al. |
| 2015/0313282 A1 | 11/2015 | Ademe et al. |
| 2015/0328415 A1 | 11/2015 | Minskoff et al. |
| 2015/0335075 A1 | 11/2015 | Minskoff et al. |
| 2015/0351456 A1 | 12/2015 | Johnson et al. |
| 2015/0359265 A1 | 12/2015 | Liu |
| 2016/0057811 A1 | 2/2016 | Alarcon et al. |
| 2016/0073694 A1 | 3/2016 | Liu |
| 2016/0091194 A1 | 3/2016 | Liu |
| 2016/0100633 A1 | 4/2016 | Gao |
| 2016/0106153 A1 | 4/2016 | Zhu |
| 2016/0135505 A1 | 5/2016 | Li et al. |
| 2016/0150828 A1 | 6/2016 | Goldstein et al. |
| 2016/0183596 A1 | 6/2016 | Rado |
| 2016/0192709 A1 | 7/2016 | Liu |
| 2016/0227837 A1 | 8/2016 | Hammel et al. |
| 2016/0242466 A1 | 8/2016 | Lord et al. |
| 2016/0262453 A1 | 9/2016 | Ampolini et al. |
| 2016/0309785 A1 | 10/2016 | Holtz |
| 2016/0309786 A1 | 10/2016 | Holtz et al. |
| 2016/0309787 A1 | 10/2016 | Hawes et al. |
| 2016/0309788 A1 | 10/2016 | Hawes et al. |
| 2016/0324216 A1 | 11/2016 | Li et al. |
| 2016/0331037 A1 | 11/2016 | Cameron |
| 2016/0345633 A1 | 12/2016 | DePiano et al. |
| 2016/0360789 A1 | 12/2016 | Hawes et al. |
| 2016/0363917 A1 | 12/2016 | Blackley |

(56) References Cited

U.S. PATENT DOCUMENTS

| | | |
|---|---|---|
| 2016/0366931 A1 | 12/2016 | Zhang |
| 2016/0366947 A1 | 12/2016 | Monsees et al. |
| 2017/0000192 A1 | 1/2017 | Li |
| 2017/0013880 A1 | 1/2017 | O'Brien et al. |
| 2017/0027227 A1 | 2/2017 | Lipowicz |
| 2017/0042240 A1 | 2/2017 | Murison |
| 2017/0064999 A1 | 3/2017 | Perez et al. |
| 2017/0079323 A1 | 3/2017 | Wang |
| 2017/0105450 A1 | 4/2017 | Reed et al. |
| 2017/0135405 A1 | 5/2017 | Reevell |
| 2017/0150757 A1 | 6/2017 | Worm et al. |
| 2017/0174914 A1 | 6/2017 | Matsumura et al. |
| 2017/0224016 A1 | 8/2017 | Reevell |
| 2017/0231283 A1 | 8/2017 | Gadas |
| 2017/0231286 A1 | 8/2017 | Borkovec et al. |
| 2017/0265523 A1 | 9/2017 | Lipowicz |
| 2017/0273354 A1 | 9/2017 | Tucker et al. |
| 2017/0325502 A1 | 11/2017 | Nelson et al. |
| 2018/0007966 A1 | 1/2018 | Li et al. |
| 2018/0027879 A1* | 2/2018 | Gavrielov .............. A24F 40/46 |
| 2018/0077967 A1* | 3/2018 | Hatton ................. A61M 11/044 |
| 2018/0161525 A1* | 6/2018 | Liu ...................... A61M 15/001 |
| 2018/0303163 A1 | 10/2018 | Baker et al. |
| 2019/0133187 A1 | 5/2019 | Spencer et al. |
| 2019/0269178 A1 | 9/2019 | Karles et al. |
| 2019/0373679 A1 | 12/2019 | Fu et al. |
| 2019/0387805 A1 | 12/2019 | Rostami |
| 2020/0029619 A1 | 1/2020 | Sundberg et al. |
| 2020/0120984 A1 | 4/2020 | Rogan |
| 2021/0176826 A1 | 6/2021 | Tucker et al. |
| 2024/0058557 A1 | 2/2024 | Alarcon et al. |

FOREIGN PATENT DOCUMENTS

| | | |
|---|---|---|
| CN | 203538371 U | 4/2014 |
| CN | 203762291 U | 8/2014 |
| CN | 104219973 A | 12/2014 |
| CN | 104244749 A | 12/2014 |
| CN | 104720115 A | 6/2015 |
| CN | 105101507 A | 11/2015 |
| CN | 105188428 A | 12/2015 |
| CN | 105455198 A | 4/2016 |
| CN | 105530825 A | 4/2016 |
| CN | 106231933 A | 12/2016 |
| CN | 106455711 A | 2/2017 |
| CN | 205947122 U | 2/2017 |
| CN | 107072293 A | 8/2017 |
| CN | 107072314 A | 8/2017 |
| CN | 107752129 A | 3/2018 |
| CN | 207613205 U | 7/2018 |
| EA | 000244 B1 | 2/1999 |
| EM | 002337410-0009 | 11/2013 |
| EM | 002337410-0012 | 11/2013 |
| EM | 002403444-0003 | 2/2014 |
| EM | 002412106-0001 | 3/2014 |
| EM | 001420327-0005 | 11/2017 |
| EP | 0973419 A1 | 1/2000 |
| EP | 2404515 A1 | 1/2012 |
| EP | 2574247 A1 | 4/2013 |
| EP | 3015010 A1 | 5/2016 |
| EP | 3075270 A1 | 10/2016 |
| EP | 3135139 A1 | 3/2017 |
| EP | 3348154 A1 | 7/2018 |
| ES | D0518506-03 | 1/2013 |
| ES | D0517952-09 | 10/2013 |
| ES | D0518082-12 | 11/2013 |
| ES | D0518097-04 | 11/2013 |
| ES | D0518201-12 | 11/2013 |
| ES | D0518036-03 | 12/2013 |
| ES | D0518299-03 | 12/2013 |
| ES | D0518462-09 | 1/2014 |
| ES | D0519904-04 | 9/2014 |
| GB | 719318 A | 12/1954 |
| GB | 4032478 | 11/2013 |
| JP | 2016-511008 A | 4/2016 |
| JP | 2017-512470 A | 5/2017 |
| JP | 3210447 U | 5/2017 |
| JP | 3213257 U | 10/2017 |
| JP | 2019-524121 A | 9/2019 |
| KR | 10-1486294 B1 | 1/2015 |
| KR | 10-2017-0044158 A | 4/2017 |
| KR | 10-2018-0048846 A | 5/2018 |
| KR | 10-2018-0083316 A | 7/2018 |
| PL | 21430-0001 | 5/2015 |
| PT | 3429-0001 | 11/2013 |
| PT | 3428-0003 | 12/2013 |
| PT | 3771-0007 | 8/2014 |
| RS | 9612-0001 | 3/2000 |
| RU | 2604313 C2 | 12/2016 |
| RU | 2607067 C2 | 1/2017 |
| RU | 2620754 C2 | 5/2017 |
| RU | 2627002 C2 | 8/2017 |
| RU | 2638514 C2 | 12/2017 |
| RU | 2639972 C2 | 12/2017 |
| RU | 2644314 C2 | 2/2018 |
| TR | 201307255-0001 | 1/2014 |
| WO | WO94/06314 A1 | 3/1994 |
| WO | WO-2007/078273 A1 | 7/2007 |
| WO | WO-2014-066730 A1 | 5/2014 |
| WO | WO-2015/027470 A1 | 3/2015 |
| WO | WO-2015/114327 A1 | 8/2015 |
| WO | WO-2015/124688 A1 | 8/2015 |
| WO | WO-2015131428 A1 | 9/2015 |
| WO | WO-2015/144822 A1 | 10/2015 |
| WO | WO-2016/065926 A1 | 5/2016 |
| WO | WO-2016/079152 A1 | 5/2016 |
| WO | WO-2016/144966 A1 | 9/2016 |
| WO | WO-2016/156509 A1 | 10/2016 |
| WO | WO-2016/172441 A1 | 10/2016 |
| WO | WO-2016/172448 A1 | 10/2016 |
| WO | WO-2016154994 A1 | 10/2016 |
| WO | WO-2016162492 A1 | 10/2016 |
| WO | WO-2017/017970 A1 | 2/2017 |
| WO | WO-2017021536 A2 | 2/2017 |
| WO | WO-2017/055802 A1 | 4/2017 |
| WO | WO-2017/084849 A1 | 5/2017 |
| WO | WO-2017/144703 A1 | 8/2017 |
| WO | WO-2017/162691 A1 | 9/2017 |
| WO | 2017/205692 A1 | 11/2017 |
| WO | WO-2017/186477 A1 | 11/2017 |
| WO | 2018/102696 A1 | 6/2018 |

OTHER PUBLICATIONS

U.S. Office Action dated Oct. 21, 2021 for corresponding U.S. Appl. No. 15/729,909.
U.S. Office Action dated Nov. 3, 2021 for corresponding U.S. Appl. No. 16/049,346.
U.S. Notice of Allowance dated Apr. 27, 2022 for corresponding U.S. Appl. No. 16/049,450.
U.S. Office Action dated May 16, 2022, for corresponding U.S. Appl. No. 16/049,346.
U.S. Office Action dated Sep. 20, 2021 for corresponding U.S. Appl. No. 16/049,450.
U.S. Office Action dated Dec. 14, 2021 for corresponding U.S. Appl. No. 16/049,450.
Russian Office Action and Search Report dated Nov. 26, 2021 for corresponding Russian Application No. 2020114678, and English-language translation thereof.
Russian Office Action and Search Report dated Nov. 25, 2021 for corresponding Russian Application No. 2020115145, and English-language translation thereof.
Russian Office Action dated Apr. 8, 2022 for corresponding Russian Application No. 2020115145, and English-language translation thereof.
Russian Notice of Allowance dated Apr. 14, 2022 for corresponding Russian Application No. 2020114678, and English-language translation thereof.
U.S. Appl. No. 15/349,377, filed Nov. 11, 2016.
"The Stunning High Tech PCC Love eCig Smart Pod Starter Kit"—http://www.sbwire.com/press-releases/the-stunning-high-tech-pcc-love-ecig-smart-pod-starter-kit-147288.htm.

(56) References Cited

OTHER PUBLICATIONS

Innokin Recommends New Electronic Cigarette to Smokers, last updated May 18, 2017.
T Spindle, "Examination of Electronic Cigarette User Puff Topography: The Effect of a Mouthpiece-Based Topography Measurement Device on Plasma Nicotine and Subjective Effects", VCU Scholars Compass, Sep. 2015.
United States Office Action for U.S. Appl. No. 15/858,425, dated Oct. 10, 2019.
Atomizer & Coil: Authentic GS-H5L 3.0 ml BCC Atomizer with LED light, http://www.ecigaretteb2c.com (Year: 2014).
United States Office Action for U.S. Appl. No. 15/729,895, dated Jan. 23, 2020.
U.S. Office Action dated Mar. 16, 2022 for corresponding U.S. Appl. No. 15/729,909.
U.S. Notice of Allowance dated Mar. 22, 2022 for corresponding U.S. Appl. No. 16/049,450.
European Office Action dated Mar. 29, 2022 for corresponding European Application No. 19752663.5.
European Notice of Allowance dated Aug. 25, 2021 for corresponding European Application No. 18829884.8.
Russian Office Action and Search Report dated Dec. 23, 2021 for corresponding Russian Application No. 2020123230, and English-language translation thereof.
Brazilian Office Action dated Aug. 9, 2022, for corresponding Brazilian Application No. BR112020005293-0, and English-language translation thereof.
U.S. Office Action dated Mar. 3, 2021 for corresponding U.S. Appl. No. 16/049,450.
U.S. Office Action dated Apr. 28, 2021 for corresponding U.S. Appl. No. 15/729,909.
Japanese Office Action dated Oct. 19, 2022, for corresponding Japanese Application No. 2020-518434, and English-language translation thereof.
U.S. Notice of Allowance dated Nov. 18, 2022, for corresponding U.S. Appl. No. 16/049,346.
U.S. Notice of Allowance dated Nov. 21, 2022, for corresponding U.S. Appl. No. 16/049,346.
U.S. Notice of Allowance dated Nov. 25, 2022, for corresponding U.S. Appl. No. 17/155,246.
Russian Office Action and Search Report dated Nov. 17, 2022, for corresponding Russian Application No. 2021104907, and English-language translation thereof.
Brazilian Office Action dated Jul. 21, 2022 for corresponding Brazilian Application No. BR112020010419-1, and English-language translation thereof.
Brazilian Office Action published in the Brazilian Industrial Property Journal dated Sep. 20, 2022, for corresponding Brazilian Application No. 112020006347-9, and English-language translation thereof.
U.S. Notice of Allowance dated Oct. 7, 2022, for corresponding U.S. Appl. No. 16/049,346.
U.S. Office Action dated Oct. 5, 2022, for corresponding U.S. Appl. No. 15/729,909.
U.S. Notice of Allowance dated Oct. 26, 2022, for corresponding U.S. Appl. No. 16/049,450.
U.S. Notice of Allowance dated Sep. 29, 2022, for corresponding U.S. Appl. No. 16/049,346.
Japanese Office Action for corresponding Application No. 2020-517203, dated Oct. 13, 2022, English translation included.
U.S. Notice of Allowance dated Dec. 14, 2022, for corresponding U.S. Appl. No. 17/155,246.
U.S. Notice of Allowance dated Dec. 27, 2022, for corresponding U.S. Appl. No. 16/049,346.
U.S. Notice of Allowance dated Dec. 27, 2022, for corresponding U.S. Appl. No. 16/049,450.
Japanese Notice of Allowance dated Jan. 30, 2023, for corresponding Japanese Application No. 2020-518434, and English-language translation thereof.
U.S. Office Action dated Feb. 15, 2023 for corresponding U.S. Appl. No. 15/729,909.
Japanese Office Action dated Dec. 12, 2022 for corresponding Japanese Application No. 2020-533704, and English-language translation thereof.
Chinese Office Action dated Jan. 29, 2023 for corresponding Chinese Application No. 201880060406.5, and English-language translation thereof.
U.S. Notice of Allowance dated Mar. 9, 2023 for corresponding U.S. Appl. No. 17/155,246.
Russian Decision to Grant and Search Report dated Mar. 1, 2023 for corresponding Russian Application No. 2021103129, and English-language translation thereof.
Office Action and Search Report dated Feb. 18, 2023 issued in related Chinese Patent Application No. 201880060418.8.
Notice of Allowance dated Mar. 13, 2023 issued in related Japanese Patent Application No. 2020-533704.
Brazilian Office Action dated Jan. 5, 2023 and published in the Brazilian Industrial Property Journal on Feb. 28, 2023 for corresponding Brazilian Application No. BR112020026871-2.
U.S. Notice of Allowance dated Apr. 3, 2023 for corresponding U.S. Appl. No. 16/049,346.
U.S. Notice of Allowance dated Mar. 31, 2023 for corresponding U.S. Appl. No. 16/049,450.
Decision to Grant dated Apr. 10, 2023 for corresponding Russian Application No. 2021104907, and English-language translation thereof.
Office Action dated May 15, 2023 issued in related Japanese patent application No. 2021-503600.
Office Action dated May 29, 2023 issued in related Japanese patent application No. 2020-517203.
Chinese Office Action dated Mar. 1, 2023 for corresponding Chinese Application No. 201880078750.7 and English-language translation thereof.
U.S. Notice of Allowance dated Jun. 29, 2023 for corresponding U.S. Appl. No. 16/049,450.
Office Action dated Jul. 13, 2023 issued in related Korean patent application No. 10-2020-7012756.
Chinese Office Action dated Jun. 28, 2023 for corresponding Chinese Application No. 201880060406.5, and English-language translation thereof.
Japanese Office Action dated Jun. 15, 2023 issued in related Japanese patent application No. 2021-500282, and English-language translation thereof.
Office Action dated Sep. 27, 2023 issued in related U.S. Appl. No. 15/729,909.
Korean Office Action dated Aug. 18, 2023 for corresponding Korean Application No. 10-2020-7012757, and English-language translation thereof.
Japanese Decision to Grant dated Oct. 5, 2023 for corresponding Japanese Application No. 2021-503600, and English-language translation thereof.
Japanese Notice of Allowance dated Oct. 26, 2023 for corresponding Japanese Application No. 2021-500282, and English-language translation thereof.
Office Action and Search Report dated Oct. 21, 2023 issued in related Chinese patent application No. 201980045676.3.
Notice of Allowance dated Nov. 8, 2023 issued in related U.S. Appl. No. 16/049,450.
Russian Notice of Allowance dated Jul. 14, 2022, for corresponding Russian Application No. 2020115145, and English-language translation thereof.
Decision of Rejection dated Dec. 4, 2023 issued in related Japanese patent application No. 2020-517203.
Notice of Allowance dated Nov. 14, 2023 issued in U.S. Appl. No. 16/049,346.
Chinese Office Action dated Nov. 9, 2023 for corresponding Chinese Application No. 201880060418.8, and English-Language translation thereof.
Chinese Office Action dated Nov. 30, 2023 for corresponding Chinese Application No. 201880078750.7, and English-language translation thereof.

(56) References Cited

OTHER PUBLICATIONS

Korean Office Action dated Nov. 24, 2023 for corresponding Korean Application No. 10- 2020-7019287, and English-language translation thereof.
Office Action dated Nov. 23, 2023 issued in related Chinese patent application No. 201980045660.2.
Russian Notice of Allowance dated Apr. 28, 2022, for corresponding Russian Application No. 2020123230. and English-language translation thereof.
Notice of Allowance dated Feb. 16, 2024 for corresponding U.S. Appl. No. 15/729,909.
Notice of Allowance issued Feb. 21, 2024 in corresponding U.S. Appl. No. 16/049,346.
Notice of Allowance issued Apr. 3, 2024 in U.S. Appl. No. 17/155,246.
Notice of Allowance issued Mar. 13, 2024 in U.S. Appl. No. 18/352,407.
Chinese Notice of Allowance for Chinese Patent Application No. 201880078750.7 mailed on Apr. 1, 2024.
Office Action dated Feb. 28, 2024 issued in Korean patent application No. 10-2020-7012756.
Notice of Allowance dated Feb. 26, 2024 issued in Korean patent application No. 10-2020-7012757.
Notice of Allowance dated Apr. 12, 2024 issued in U.S. Appl. No. 16/049,450.
Notice of Allowance dated Apr. 25, 2024 issued in U.S. Appl. No. 15/729,909.
Office Action dated Mar. 31, 2024 issued in Chinese patent application No. 201880060418.8.
Korea Notice of Allowance for Korean Patent Application No. 10-2020-7019287 dated May 1, 2024 and English translation thereof.
Notice of Allowance issued May 22, 2024 in U.S. Appl. No. 17/155,246.
Notice of Allowance issued Jun. 11, 2024 in U.S. Appl. No. 16/049,346.
Office Action dated Jun. 13, 2024 in U.S. Appl. No. 18/480,586.
Notice of Allowance dated Jun. 17, 2024 issued in Japanese Patent Application No. 2020-517203.
Notice of Allowance dated Jul. 22, 2024 issued in U.S. Appl. No. 15/729,909.
Notice of Allowance dated Aug. 28, 2024 issued in U.S. Appl. No. 15/729,909.
Notice of Allowance dated Nov. 12, 2024 issued in U.S. Appl. No. 15/729,909.
Office Action mailed Aug. 20, 2024 issued in Brazilian Patent Application No. 1120200052930.
Notice of Allowance dated Sep. 18, 2024 issued in U.S. Appl. No. 16/049,346.
Office Action dated Aug. 7, 2024 issued in U.S. Appl. No. 18/411,538.
Notice of Allowance dated Aug. 7, 2024 issued in U.S. Appl. No. 16/049,346.
Office Action dated Sep. 26, 2024 issued in U.S. Appl. No. 18/480,586.
Notice of Allowance dated Oct. 1, 2024 issued in U.S. Appl. No. 17/893,614.
Office Action dated Sep. 14, 2024 issued in Korean patent application No. 10-2021-7004399.
Notice of Allowance dated Jul. 24, 2024 issued in Korean patent application No. 10-2020-7012756.
Notice of Allowance dated Nov. 27, 2024 issued in U.S. Appl. No. 16/049,346.
Notice of Allowance dated Dec. 2, 2024 issued in U.S. Appl. No. 16/049,450.
Extended European Search Report for European Patent Application No. 24196619.1 issued on Dec. 9, 2024.
Notice of Allowance dated Dec. 18, 2024 issued in U.S. Appl. No. 18/411,538.
Notice of Allowance dated Dec. 20, 2024 issued in U.S. Appl. No. 18/411,538.
Office Action dated Jan. 13, 2025 issued in U.S. Appl. No. 18/480,586.
Corrected Notice of Allowability dated Jan. 22, 2025 issued in U.S. Appl. No. 16/049,346.
Result of Consultation dated Jun. 5, 2024 issued in European Patent Application No. 19752663.5.
Notice of Allowance dated Jun. 20, 2024 issued in Chinese Patent Application No. 201880060418.8.
Office Action dated Jun. 26, 2024 issued in U.S. Appl. No. 16/049,450.
Decision to Refuse dated Jun. 27, 2024 issued in European patent application No. 19752663.5.
Notice of Allowance dated Mar. 11, 2025 issued in U.S. Appl. No. 18/411,538.
U.S. Appl. No. 15/349,377 filed on Nov. 11, 2016.
United States Office Action for corresponding U.S. Appl. No. 29/621,730 dated Dec. 17, 2018.
International Search Report and Written Opinion thereof dated Jan. 22, 2019 for corresponding International Application No. PCT/EP2018/077806.
Innokin Recommends New Electronic Cigareete toSmokes, last updated May 18, 2017.
T Spindle, "Examination of Electronic Cigarette User Puff Topography: The Effect of a Mouthpiece-Based Topography Measurement Device on Palsma Nicotine and Subjective Effects", VCU Scholars Compass, Sep. 2015.
International Search Report and Written Opinion thereof dated Jan. 21, 2019 for corresponding International Application No. PCT/EP2018/077799.
International Search Report and Written Opinion dated Mar. 20, 2019 for corresponding International Application No. PCT/EP2018/086849.
United States Notice of Allowance for U.S. Appl. No. 29/621,730, dated Aug. 14, 2019.
United States Office Action for U.S. Appl. No. 15/858,425, dated Aug. 14, 2019.
International Search Report and Written Opinion thereof dated Nov. 22, 2019 for corresponding International Application No. PCT/EP2019/070556.
International Search Report and Written Opinion for corresponding Application No. PCT/EP2019/070556, dated Nov. 22, 2019.
International Search Report and Written Opinion thereof dated Dec. 12, 2019 for corresponding International Application No. PCT/EP2019/070559.
International Search Report and Written Opinion for corresponding Application No. PCT/EP2019/070559, dated Dec. 12, 2019.
U.S. Office Action dated Jan. 23, 2020 for corresponding U.S. Appl. No. 15/729,895.
U.S. Notice of Allowance dated Jan. 29, 2020 for corresponding U.S. Appl. No. 15/858,425.
Atmozier & Coil: Authentic GS-H5L 3.0 ml BCC Atomizer with LED light, http://www.ecigaretteb2c.com (Year: 2014).
U.S. Appl. No. 15/729,895, dated Jan. 23, 2020.
U.S. Notice of Allowance dated Feb. 24, 2020 for corresponding U.S. Appl. No. 15/858,425.
International Preliminary Report on Patentability dated Apr. 23, 2020 for corresponding International Application No. PCT/EP2018/077806.
U.S. Notice of Allowance dated May 6, 2020 for corresponding U.S. Appl. No. 15/729,895.
Written Opinion of the International Preliminary Examining Authority dated Jun. 10, 2020 for corresponding International Application No. PCT/EP2019/070559.
Written Opinion for corresponding International Application No. PCT/EP2019/070559, dated Jun. 10, 2020.
International Preliminary Report on Patentability dated Jun. 30, 2020 for corresponding International Application No. PCT/EP2019/070556.
International Preliminary Report on Patentability for corresponding Application No. PCT/EP2019/070556, dated Jun. 30, 2020.
International Preliminary Report on Patentability and Written Opinion thereof dated Jul. 9, 2020 for corresponding International Application No. PCT/EP2018/086849.
Notice of Allowance dated Feb. 24, 2025 issued in Korean patent application No. 10-2021-7004399.
Notice of Allowance dated Feb. 8, 2025 issued in Korean patent application No. 10-2021-7004862.

(56) References Cited

OTHER PUBLICATIONS

Notice of Allowance dated Mar. 24, 2025 issued in U.S. Appl. No. 17/893,614.
Notice of Allowance dated Apr. 14, 2025 issued in U.S. Appl. No. 16/049,450.

* cited by examiner

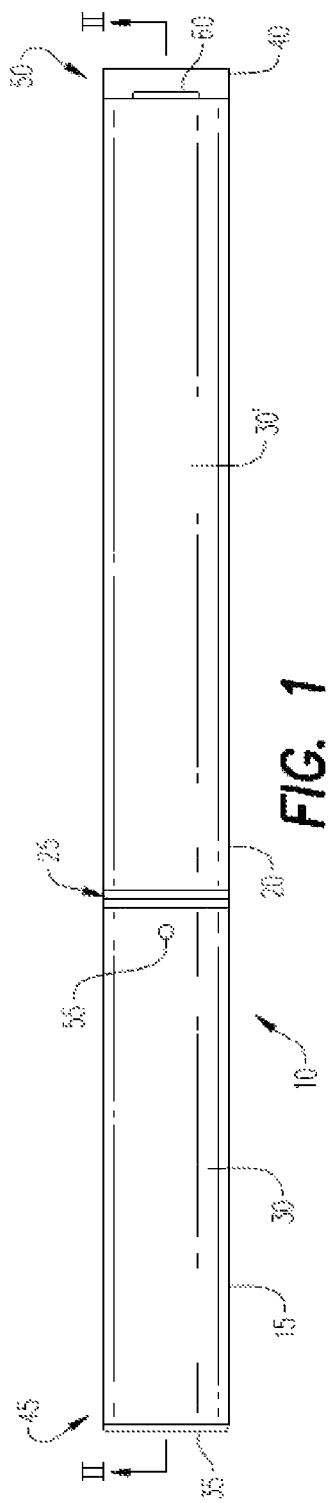
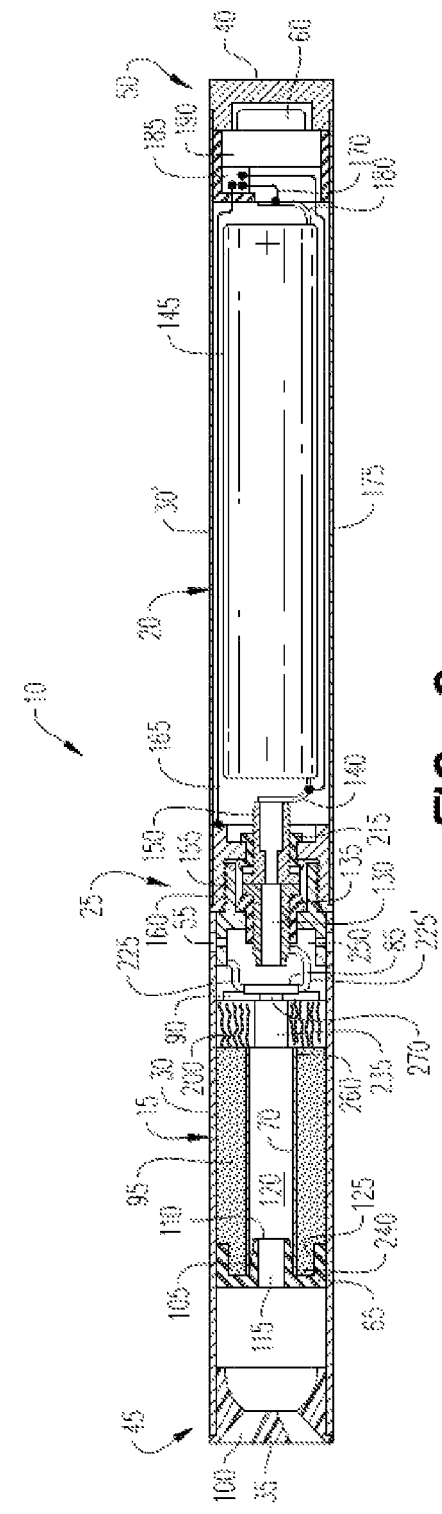
FIG. 1
FIG. 2

FIG. 4

ELECTRONIC VAPING DEVICE INCLUDING TRANSFER PAD WITH ORIENTED FIBERS

CROSS-REFERENCE TO RELATED APPLICATION

This application is a continuation application of U.S. application Ser. No. 15/729,895, filed Oct. 11, 2017, the entire content of which is incorporated herein by reference thereto.

BACKGROUND

Field

The present disclosure relates to an electronic vaping or e-vaping device.

Description of Related Art

An e-vaping device includes a heater element which vaporizes a pre-vapor formulation to produce a "vapor."

The e-vaping device includes a power supply, such as a rechargeable battery, arranged in the device. The battery is electrically connected to the heater, such that the heater heats to a temperature sufficient to convert a pre-vapor formulation to a vapor. The vapor exits the e-vaping device through a mouthpiece including at least one outlet.

SUMMARY

At least one example embodiment relates to a cartridge of an electronic vaping device.

In at least one example embodiment, a cartridge for an electronic vaping device comprises an outer housing extending in a longitudinal direction and a reservoir configured to contain a pre-vapor formulation. The reservoir is in the outer housing. The reservoir has a first reservoir end and a second reservoir end. The cartridge also includes a seal at the first reservoir end, a transfer pad at the second reservoir end, and a wick in contact with the transfer pad. The transfer pad includes a plurality of fibers. Each of the plurality of fibers is substantially parallel to the longitudinal direction.

In at least one example embodiment, the reservoir is under atmospheric pressure.

In at least one example embodiment, the transfer pad has a density ranging from about 0.08 g/cc to about 0.3 g/cc.

In at least one example embodiment, the transfer pad has a length of about 5.0 mm to about 10.0 mm and a density of about 0.08 g/cc to about 0.1 g/cc.

In at least one example embodiment, the transfer pad has a length of about 0.5 mm to about 5.0 mm and a density of about 0.1 g/cc to about 0.3 g/cc.

In at least one example embodiment, the transfer pad includes a plurality of channels. Each of the plurality of channels is between adjacent ones of the plurality of fibers.

In at least one example embodiment, the transfer pad includes an outer side wall. The outer side wall has a coating thereon.

In at least one example embodiment, the transfer pad has a length ranging from about 0.5 mm to about 10.0 mm.

In at least one example embodiment, the cartridge further includes an inner tube within the outer housing. The reservoir is between an outer surface of the inner tube and an inner surface of the outer housing.

In at least one example embodiment, the transfer pad defines a channel extending through the transfer pad. The channel is sized and configured to fit around the outer surface of the inner tube at the second end of the reservoir.

In at least one example embodiment, the plurality of fibers includes at least one of polypropylene and polyester.

In at least one example embodiment, the cartridge further includes at least one heater in fluid communication with the wick. The at least one heater does not contact the transfer pad.

In at least one example embodiment, about 50% to about 100% of the plurality of fibers extend substantially in the longitudinal direction. In at least one example embodiment, about 75% to about 95% of the plurality of fibers extend substantially in the longitudinal direction.

At least one example embodiment relates to an electronic vaping device.

In at least one example embodiment, an electronic vaping device comprises an outer housing extending in a longitudinal direction and a reservoir configured to contain a pre-vapor formulation. The reservoir is in the outer housing, and the reservoir has a first reservoir end and a second reservoir end. The electronic vaping device also includes a seal at the first reservoir end, a transfer pad at the second reservoir end, a wick in contact with the transfer pad, at least one heater in fluid communication with the wick, and a power supply electrically connectable to the at least one heater. The transfer pad includes a plurality of fibers. The plurality of fibers is substantially parallel to the longitudinal direction.

In at least one example embodiment, the reservoir is under atmospheric pressure.

In at least one example embodiment, the transfer pad has a density ranging from about 0.08 g/cc to about 0.3 g/cc.

In at least one example embodiment, the transfer pad has a length of about 5.0 mm to about 10.0 mm and a density of about 0.08 g/cc to about 0.1 g/cc.

In at least one example embodiment, the transfer pad has a length of about 0.5 mm to about 5.0 mm and a density of about 0.1 g/cc to about 0.3 g/cc.

In at least one example embodiment, the transfer pad includes a plurality of channels. Each of the plurality of channels is between adjacent ones of the plurality of fibers.

In at least one example embodiment, the transfer pad includes an outer side wall. The outer side wall has a coating thereon.

In at least one example embodiment, the transfer pad has a length ranging from about 0.5 mm to about 10.0 mm.

In at least one example embodiment, the electronic vaping further comprises an inner tube within the outer housing. The reservoir is between an outer surface of the inner tube and an inner surface of the outer housing. The transfer pad is between the outer surface of the inner tube and the inner surface of the outer housing.

In at least one example embodiment, the transfer pad defines a channel extending through the transfer pad, and the channel is sized and configured to fit around the outer surface of the inner tube at the second end of the reservoir.

In at least one example embodiment, the plurality of fibers includes at least one of polypropylene and polyester.

In at least one example embodiment, the at least one heater does not contact the transfer pad.

In at least one example embodiment, about 50% to about 100% of the plurality of fibers extend substantially in the longitudinal direction. In at least one example embodiment, about 75% to about 95% of the plurality of fibers extend substantially in the longitudinal direction.

At least one example embodiment relates to a method of forming a cartridge of an electronic vaping device.

In at least one example embodiment, a method of forming a cartridge of an electronic vaping device comprises positioning an inner tube within an outer housing to establish a reservoir between an outer surface of the inner tube and an inner surface of the outer housing, the inner tube defining an air passage therethrough; inserting a gasket at a first end of the inner tube, the gasket defining a channel in communication with the air passage, the gasket sealing a first reservoir end; and positioning a transfer pad at a second end of the inner tube, the transfer pad including a plurality of fibers, the plurality of fibers being substantially parallel to the longitudinal direction.

In at least one example embodiment, the transfer pad has an outer diameter that is larger than an inner diameter of the outer housing.

In at least one example embodiment, the transfer pad is formed by a melt blowing process.

In at least one example embodiment, the method further comprises positioning a mouth-end insert at a first end of the outer housing.

In at least one example embodiment, the method also includes positioning a wick in contact with the transfer pad; and positioning a heater in contact with the wick, the heater not in physical contact with the transfer pad.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1 is a side view of an electronic vaping device according to at least on example embodiment.

FIG. 2 is a cross-sectional view along line II-II of the electronic vaping device of FIG. 1 according to at least one example embodiment.

FIG. 4 is a graph comparing electronic vaping devices including transfer pads having different densities and/or lengths according to at least one example embodiment.

DETAILED DESCRIPTION OF EXAMPLE EMBODIMENTS

Figure 3A:
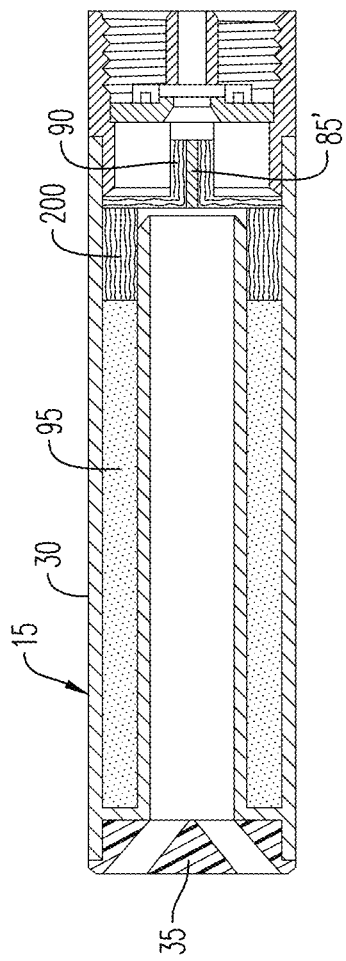
FIG. 3A is a cross-sectional view of a cartridge according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a side view of an e-vaping device according to at least one example embodiment.

In at least one example embodiment, as shown in FIG. 1, an electronic vaping device (e-vaping device) 10 may include a replaceable cartridge (or first section) 15 and a reusable battery section (or second section) 20, which may be coupled together at a threaded connector 25. It should be appreciated that the connector 25 may be any type of connector, such as a snug-fit, detent, clamp, bayonet, and/or clasp. An air inlet 55 extends through a portion of the connector 25.

In at least one example embodiment, the connector 25 may be the connector described in U.S. application Ser. No. 15/154,439, filed May 13, 2016, the entire contents of which is incorporated herein by reference thereto. As described in U.S. application Ser. No. 15/154,439, the connector 25 may be formed by a deep drawn process.

In at least one example embodiment, the first section 15 may include a first housing 30 and the second section 20 may include a second housing 30'. The e-vaping device 10 includes a mouth-end insert 35 at a first end 45.

In at least one example embodiment, the first housing 30 and the second housing 30' may have a generally cylindrical cross-section. In other example embodiments, the housings 30 and 30' may have a generally triangular cross-section along one or more of the first section 15 and the second section 20. Furthermore, the housings 30 and 30' may have the same or different cross-section shape, or the same or different size. As discussed herein, the housings 30, 30' may also be referred to as outer or main housings.

In at least one example embodiment, the e-vaping device 10 may include an end cap 40 at a second end 50 of the e-vaping device 10. The e-vaping device 10 also includes a light 60 between the end cap 40 and the first end 45 of the e-vaping device 10.

FIG. 2 is a cross-sectional view along line II-II of the e-vaping device of FIG. 1.

In at least one example embodiment, as shown in FIG. 2, the first section 15 may include a reservoir 95 configured to store a pre-vapor formulation and a vaporizer 80 that may vaporize the pre-vapor formulation. The vaporizer 80 incudes a heating element 85 and a wick 90. The wick 90 may draw the pre-vapor formulation from the reservoir 95. The heating element 85 may be a planar heating element including a filament portion, and the wick 90 may be a disk of wicking material as described in U.S. Patent Publication No. 2016/0309786 to Holtz et al. filed on Apr. 22, 2016, the entire content of which is incorporated herein by reference.

The e-vaping device 10 may include the features set forth in U.S. Patent Application Publication No. 2013/0192623 to Tucker et al. filed Jan. 31, 2013, the entire contents of each of which are incorporated herein by reference thereto. In other example embodiments, the e-vaping device may include the features set forth in U.S. Patent Application Publication No. 2016/0309785 filed Apr. 22, 2016, and/or U.S. Pat. No. 9,289,014 issued Mar. 22, 2016, the entire contents of each of which is incorporated herein by reference thereto.

In at least one example embodiment, the pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, plant material, natural or artificial flavors, and/or vapor formers such as glycerin and propylene glycol. The plant material may include tobacco and/or non-tobacco plant material.

In at least one example embodiment, the first section 15 may include the housing 30 extending in a longitudinal direction and an inner tube (or chimney) 70 coaxially positioned within the housing 30. The inner tube 70 has a first end 240 and a second end 260.

A transfer pad 200 abuts the second end 260 of the inner tube 70. An outer perimeter of the transfer pad 200 may provide a seal with an interior surface of the housing 30. The transfer pad 200 reduces and/or prevents leakage of liquid from the reservoir 95 that is established between the inner tube 70 and the housing 30.

In at least one example embodiment, the transfer pad 200 includes a central, longitudinal air passage 235 defined therein. The air passage 235 is in fluid communication with an inner passage (also referred to as a central channel or central inner passage) 120 defined by the inner tube 70.

In at least one example embodiment, the transfer pad 200 includes a plurality of fibers. Each of the plurality of fibers is substantially parallel to the longitudinal direction. The transfer pad 200 may be formed of at least one of polypropylene and polyester. In at least one example embodiment, the transfer pad 200 may be formed of polyolefin. Other polymers may be used to form the transfer pad 200.

The transfer pad 200 may be formed by a melt blowing process, where micro- and/or nano-fibers are formed from at least one polymer that is melted and extruded through small nozzles surrounded by high speed blowing gas and/or air.

The polymers used in the melt blowing process do not include any processing aids, such as antistatics, lubricants, bonding agents, and/or surfactants. Thus, the polymers are substantially pure and the transfer pad 200 is inert to the pre-vapor formulation. In other example embodiments, the polymers may be mixed with processing aids, such as antistatics, lubricants, bonding agents, and/or surfactants. The transfer pad 200 may be obtained from Essentra PLC.

In at least one example embodiment, the transfer pad 200 includes an outer side wall. The outer side wall may have a coating thereon that aids in reducing leakage and/or forming a seal between the transfer pad 200 and an inner surface of the housing 30. The coating may include a hydrophobic or hydrophilic surface texture and/or be a parylene coating.

While not wishing to be bound by theory, melt blowing polymers to form the transfer pad 200 may provide a melted outer surface that also aids in reducing leakage.

In at least one example embodiment, the transfer pad 200 includes a plurality of channels. Each of the plurality of channels is between adjacent ones of the plurality of fibers. The channels may have a diameter ranging from about 0.01 mm to about 0.3 mm (e.g., about 0.02 mm to about 0.2 mm, about 0.03 mm to about 0.1 mm, about 0.04 mm to about 0.09 mm, or about 0.05 mm to about 0.08 mm).

In at least one example embodiment, about 50% to about 100% (e.g., about 55% to about 95%, about 60% to about 90%, about 65% to about 85%, or about 70% to about 75%) of the plurality of fibers extend substantially in the longitudinal direction. In at least one example embodiment, about 75% to about 95% (e.g., about 80% to about 90% or about 82% to about 88%) of the plurality of fibers extend substantially in the longitudinal direction.

The transfer pad may be generally cylindrical or disc shaped, but the transfer pad is not limited to cylindrical or disc shaped forms and a shape of the transfer pad may depend on a shaped of the reservoir and housing. An outer diameter of the transfer pad 200 may range from about 3.0 mm to about 20.0 mm (e.g., about 5.0 mm to about 18.0 mm, about 7.0 mm to about 15.0 mm, about 9.0 mm to about 13.0 mm, or about 10.0 mm to about 12.0 mm). The air passage 235 within the transfer pad 200 may have an inner diameter that is substantially the same as an inner diameter of the inner tube 70. In at least one example embodiment, the inner diameter of the air passage 235 ranges from about 1.0 mm to about 10.0 mm (about 2.0 mm to about 8.0 mm or about 4.0 mm to about 8.0 mm).

In at least one example embodiment, the transfer pad 200 is oriented, such that the channels mostly transverse to the longitudinal direction of the housing 30. In other example embodiments, the transfer pad 200 is oriented, such that the channels do not run transverse to the longitudinal direction of the housing 30.

While not wishing to be bound by theory, it is believed that the pre-vapor formulation travels through the channels, and a diameter of the channels is such that a liquid surface tension and pressurization within the reservoir moves and holds the pre-vapor formulation within the channel without leaking.

In at least one example embodiment, the transfer pad 200 may be in a vaping device that does not include a reservoir in a closed system and/or at atmospheric pressure.

In at least one example embodiment, the reservoir is sealed at a first end thereof and the transfer pad 200 is at a second end thereof.

In at least one example embodiment, the transfer pad 200 has a density ranging from about 0.08 g/cc to about 0.3 g/cc (e.g., about 0.01 g/cc to about 0.25 g/cc or about 0.1 g/cc to about 0.2 g/cc). The transfer pad 200 has a length ranging from about 0.5 millimeter (mm) to about 10.0 mm (e.g., about 1.0 mm to about 9.0 mm, about 2.0 mm to about 8.0 mm, about 3.0 mm to about 7.0 mm, or about 4.0 mm to about 6.0 mm). In at least one example embodiment, as the density of the transfer pad 200 increases, the length of the transfer pad decreases. Thus, transfer pads 200 having lower densities within the above-referenced range may be longer than transfer pads 200 having higher densities.

In at least one example embodiment, the transfer pad 200 has a length of about 5.0 mm to about 10.0 mm and a density of about 0.08 g/cc to about 0.1 g/cc.

In at least one example embodiment, the transfer pad 200 has a length of about 0.5 mm to about 5.0 mm and a density of about 0.1 g/cc to about 0.3 g/cc.

In at least one example embodiment, the density and/or length of the transfer pad 200 is chosen based on the viscosity of a liquid flowing therethrough. Moreover, the density of the transfer pad 200 is chosen based on desired vapor mass, desired flow rate of the pre-vapor formulation flow rate, and the like.

In at least one example embodiment, the first connector piece 155 may include a male threaded section for effecting the connection between the first section 15 and the second section 20.

In at least one example embodiment, at least two air inlets 55 may be included in the housing 30. Alternatively, a single air inlet 55 may be included in the housing 30. Such arrangement allows for placement of the air inlet 55 close to the connector 25 without occlusion by the presence of the first connector piece 155. This arrangement may also reinforce the area of air inlets 55 to facilitate precise drilling of the air inlets 55.

In at least one example embodiment, the air inlets 55 may be provided in the connector 25 instead of in the housing 30. In other example embodiments, the connector 25 may not include threaded portions.

In at least one example embodiment, the at least one air inlet 55 may be formed in the housing 30, adjacent the connector 25 to reduce and/or minimize the chance of an adult vaper's fingers occluding one of the ports and to control the resistance-to-draw (RTD) during vaping. In at least one example embodiment, the air inlet 55 may be machined into the housing 30 with precision tooling such that their diameters are closely controlled and replicated from one e-vaping device 10 to the next during manufacture.

In at least one example embodiment, the air inlets 55 may be sized and configured such that the e-vaping device 10 has a resistance-to-draw (RTD) in the range of from about 60 mm $H_2O$ to about 150 mm $H_2O$.

In at least one example embodiment, a nose portion 110 of a gasket 65 may be fitted into a first end portion 105 of the inner tube 70. An outer perimeter of the gasket 65 may provide a substantially tight seal with an inner surface 125 of the housing 30. The gasket 65 may include a central channel 115 disposed between the inner passage 120 of the inner tube 70 and the interior of the mouth-end insert 35, which may transport the vapor from the inner passage 120 to the mouth-end insert 35. The mouth-end insert 35 includes at least two outlets 100, which may be located off-axis from the longitudinal axis of the e-vaping device 10. The outlets 100 may be angled outwardly in relation to the longitudinal axis of the e-vaping device 10. The outlets 100 may be substantially uniformly distributed about the perimeter of the mouth-end insert 35 so as to substantially uniformly distribute vapor.

In at least one example embodiment, the space defined between the gasket 65, the transfer pad 200, the housing 30, and the inner tube 70 may establish the confines of the reservoir 95. The reservoir 95 may contain the pre-vapor formulation, and optionally a storage medium (not shown) configured to store the pre-vapor formulation therein. The storage medium may include a winding of cotton gauze or other fibrous material about the inner tube 70. The reservoir is under atmospheric pressure.

In at least one example embodiment, the reservoir 95 may at least partially surround the inner passage 120. Thus, the reservoir 95 may at least partially surround the inner passage 120. The heating element 85 may extend transversely across the inner passage 120 between opposing portions of the reservoir 95. In some example embodiments, the heater 85 may extend parallel to a longitudinal axis of the inner passage 120.

In at least one example embodiment, the reservoir 95 may be sized and configured to hold enough pre-vapor formulation such that the e-vaping device 10 may be configured for vaping for at least about 200 seconds. Moreover, the e-vaping device 10 may be configured to allow each puff to last a maximum of about 5 seconds.

In at least one example embodiment, the storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In at least one example embodiment, the reservoir 95 may include a filled tank lacking any storage medium and containing only pre-vapor formulation.

During vaping, pre-vapor formulation may be transferred from the reservoir 95 and/or storage medium to the proximity of the heating element 85 via capillary action of the wick 90, which pulls the pre-vapor formulation from the transfer pad 200. The wick 90 may be a generally tubular, and may define an air channel 270 therethrough. The heating element 85 abuts one end of the wick 90. In other example embodiment, the heating element may at least partially surround a portion of the wick 90. When the heating element 85 is activated, the pre-vapor formulation in the wick 90 may be vaporized by the heating element 85 to form a vapor.

In at least one example embodiment, the wick 90 is in direct physical contact with the transfer pad 200, but the heating element 85 does not directly contact the transfer pad 200. In other example embodiments, the heating element 85 may contact the wick 90 and the transfer pad 200 (not shown).

In at least one example embodiment, the wick 90 includes one or more layers of a sheet of wicking material. The sheet of wicking material may be formed of borosilicate or glass fiber. The sheet of wicking material may be folded and/or the wick 90 includes two or more layers of the sheet of wicking material. The sheet of wicking material may have a thickness ranging from about 0.2 mm to about 2.0 mm (e.g., about 0.3 mm to about 1.75 mm, about 0.5 mm to about 1.5 mm, or about 0.75 mm to about 1.0 mm).

In other example embodiments, the wick 90 may include filaments (or threads) having a capacity to draw the pre-vapor formulation. For example, the wick 90 may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 10. In at least one example embodiment, the wick 90 may include one to eight filament strands, each strand comprising a plurality of glass filaments twisted together. The end portions of the wick 90 may be flexible and foldable into the confines of the reservoir 95. The filaments may have a cross-section that is generally cross-shaped, clover-shaped, Y-shaped, or in any other suitable shape.

In at least one example embodiment, the wick 90 may include any suitable material or combination of materials. Examples of suitable materials may be, but not limited to, glass, ceramic- or graphite-based materials. The wick 90 may have any suitable capillarity drawing action to accommodate pre-vapor formulations having different physical properties such as density, viscosity, surface tension and vapor pressure. The wick 90 may be non-conductive.

In at least one example embodiment, the heating element 85 may include a planar sheet of metal that abuts the wick 90. The planar sheet may extend fully or partially along the length of the wick 90. In some example embodiments, the heating element 85 may not be in contact with the wick 90.

In other example embodiment, not shown, the heating element 85 can be in the form of a wire coil, a ceramic body, a single wire, a cage of resistive wire, or any other suitable form. The heating element 85 may be any heater that is configured to vaporize a pre-vapor formulation.

In at least one example embodiment, the heating element 85 may be formed of any suitable electrically resistive materials. Examples of suitable electrically resistive materials may include, but not limited to, copper, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 85 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 85 may include at least one material selected from the group consisting of stainless steel, copper, copper alloys, nickel-chromium alloys, super alloys and combinations thereof. In an example embodiment, the heating element 85 may be formed of nickel-chromium alloys or iron-chromium alloys. In another example embodiment, the heating element 85 may be a ceramic heater having an electrically resistive layer on an outside surface thereof.

The inner tube 70 may include a pair of opposing slots, such that the wick 90 and the first and second electrical leads 225, 225' or ends of the heating element 85 may extend out from the respective opposing slots. The provision of the opposing slots in the inner tube 70 may facilitate placement of the heating element 85 and wick 90 into position within the inner tube 70 without impacting edges of the slots and the coiled section of the heating element 85. Accordingly, edges of the slots may not be allowed to impact and alter the coil spacing of the heating element 85, which would otherwise create potential sources of hotspots. In at least one example embodiment, the inner tube 70 may have a diameter of about 4 mm and each of the opposing slots may have major and minor dimensions of about 2 mm by about 4 mm.

In at least one example embodiment, the first lead 225 is physically and electrically connected to the male threaded connector piece 155. As shown, the male threaded first connector piece 155 is a hollow cylinder with male threads on a portion of the outer lateral surface. The connector piece is conductive, and may be formed or coated with a conductive material. The second lead 225' is physically and electrically connected to a first conductive post 130. The first conductive post 130 may be formed of a conductive material (e.g., stainless steel, copper, etc.), and may have a T-shaped cross-section as shown in FIG. 2. The first conductive post 130 nests within the hollow portion of the first connector piece 155, and is electrically insulated from the first connector piece 155 by an insulating shell 135. The first conductive post 130 may be hollow as shown, and the hollow portion may be in fluid communication with the air passage 120. Accordingly, the first connector piece 155 and the first conductive post 130 form respective external electrical connection to the heating element 85.

In at least one example embodiment, the heating element 85 may heat pre-vapor formulation in the wick 90 by thermal conduction. Alternatively, heat from the heating element 85 may be conducted to the pre-vapor formulation by means of a heat conductive element or the heating element 85 may transfer heat to the incoming ambient air that is drawn through the e-vaping device 10 during vaping, which in turn heats the pre-vapor formulation by convection.

It should be appreciated that, instead of using a wick 90, the heating element 85 may include a porous material which incorporates a resistance heater formed of a material having a high electrical resistance capable of generating heat quickly.

As shown in FIG. 2, the second section 20 includes a power supply 145, a control circuit 185, and a sensor 190. As shown, the control circuit 185 and the sensor 190 are disposed in the housing 30'. A female threaded second connector piece 160 forms a second end. As shown, the second connector piece 160 has a hollow cylinder shape with threading on an inner lateral surface. The inner diameter of the second connector piece 160 matches that of the outer diameter of the first connector piece 155 such that the two connector pieces 155, 160 may be threaded together to form the connection 25. Furthermore, the second connector piece 160, or at least the other lateral surface is conductive, for example, formed of or including a conductive material. As such, an electrical and physical connection occurs between the first and second connector pieces 155, 160 when connected.

As shown, a first lead 165 electrically connects the second connector piece 160 to the control circuit 185. A second lead 170 electrically connects the control circuit 185 to a first terminal 180 of the power supply 145. A third lead 175 electrically connects a second terminal 140 of the power supply 145 to the power terminal of the control circuit 185 to provide power to the control circuit 185. The second terminal 140 of the power supply 145 is also physically and electrically connected to a second conductive post 150. The second conductive post 150 may be formed of a conductive material (e.g., stainless steel, copper, etc.), and may have a T-shaped cross-section as shown in FIG. 2. The second conductive post 150 nests within the hollow portion of the second connector piece 160, and is electrically insulated from the second connector piece 160 by a second insulating shell 215. The second conductive post 150 may also be hollow as shown. When the first and second connector pieces 155, 160 are mated, the second conductive post 150 physically and electrically connects to the first conductive post 130. Also, the hollow portion of the second conductive post 150 may be in fluid communication with the hollow portion of the first conductive post 130.

While the first section 15 has been shown and described as having the male connector piece and the second section 20 has been shown and described as having the female connector piece, an alternative embodiment includes the opposite where the first section 15 has the female connector piece and the second section 20 has the male connector piece.

In at least one example embodiment, the power supply 145 includes a battery arranged in the e-vaping device 10. The power supply 145 may be a Lithium-ion battery or one of its variants, for example a Lithium-ion polymer battery. Alternatively, the power supply 145 may be a nickel-metal hydride battery, a nickel cadmium battery, a lithium-manganese battery, a lithium-cobalt battery or a fuel cell. The e-vaping device 10 may be vapable by an adult vaper until the energy in the power supply 145 is depleted or in the case of lithium polymer battery, a minimum voltage cut-off level is achieved.

In at least one example embodiment, the power supply 145 is rechargeable. The second section 20 may include circuitry configured to allow the battery to be chargeable by an external charging device. To recharge the e-vaping device 10, an USB charger or other suitable charger assembly may be used as described below.

In at least one example embodiment, the sensor 190 is configured to generate an output indicative of a magnitude and direction of airflow in the e-vaping device 10. The control circuit 185 receives the output of the sensor 190, and determines if (1) the direction of the airflow indicates a draw on the mouth-end insert 8 (versus blowing) and (2) the magnitude of the draw exceeds a threshold level. If these vaping conditions are met, the control circuit 185 electrically connects the power supply 145 to the heating element 85; thus, activating the heating element 85. Namely, the control circuit 185 electrically connects the first and second leads 165, 170 (e.g., by activating a heater power control transistor forming part of the control circuit 185) such that the heating element 85 becomes electrically connected to the power supply 145. In an alternative embodiment, the sensor 190 may indicate a pressure drop, and the control circuit 185 activates the heating element 85 in response thereto.

In at least one example embodiment, the control circuit 185 may also include a light 60, which the control circuit 185 activates to glow when the heating element 85 is activated and/or the battery 145 is recharged. The light 60 may include one or more light-emitting diodes (LEDs). The LEDs may include one or more colors (e.g., white, yellow, red, green, blue, etc.). Moreover, the light 60 may be arranged to be visible to an adult vaper during vaping, and may be positioned between the first end 45 and the second end 50 of the e-vaping device 10. In addition, the light 60 may be utilized for e-vaping system diagnostics or to indicate that recharging is in progress. The light 60 may also be configured such that the adult vaper may activate and/or deactivate the heater activation light 60 for privacy.

In at least one example embodiment, the control circuit 185 may include a time-period limiter. In another example embodiment, the control circuit 185 may include a manually operable switch for an adult vaper to initiate heating. The time-period of the electric current supply to the heating element 85 may be set or pre-set depending on the amount of pre-vapor formulation desired to be vaporized.

Next, operation of the e-vaping device to create a vapor will be described. For example, air is drawn primarily into the first section 15 through the at least one air inlet 55 in response to a draw on the mouth-end insert 35. The air passes through the air inlet 55, into the space 250, through the air channel 270, through the central passage 235, into the inner passage 120, and through the outlet 100 of the mouth-end insert 35. If the control circuit 185 detects the vaping conditions discussed above, the control circuit 185 initiates power supply to the heating element 85, such that the heating element 85 heats pre-vapor formulation in the wick 90. The vapor and air flowing through the inner passage 120 combine and exit the e-vaping device 10 via the outlet 100 of the mouth-end insert 35.

When activated, the heating element 85 may heat a portion of the wick 90 for less than about 10 seconds.

In at least one example embodiment, the first section 15 may be replaceable. In other words, once the pre-vapor formulation of the cartridge is depleted, only the first section 15 may be replaced. An alternate arrangement may include an example embodiment where the entire e-vaping device 10 may be disposed once the reservoir 95 is depleted. In at least one example embodiment, the e-vaping device 10 may be a one-piece e-vaping device.

In at least one example embodiment, the e-vaping device 10 may be about 80 mm to about 110 mm long and about 7 mm to about 8 mm in diameter. For example, in one example embodiment, the e-vaping device 10 may be about 84 mm long and may have a diameter of about 7.8 mm.

FIG. 3A is a cross-sectional view of a cartridge according to at least one example embodiment.

In at least one example embodiment, as shown in FIG. 3A, the first section 15 includes the transfer pad 200 that abuts the wick 90, and the heater 85' is folded around three sides of the wick 90.

In at least one example embodiment, the wick 90 may include one or more sheets of material, such as a sheet formed of borosilicate fibers. The sheet of material may be folded, braided, twisted, adhered together, etc. to form the wick 90. The sheet of material may include one or more layers of material. The sheet of material may be folded and/or twisted. If multiple layers of material are included, each layer may have a same density or a different density than other layers. The layers may have a same thickness or a different thickness. The wick 90 may have a thickness ranging from about 0.2 mm to about 2.0 mm (e.g., about 0.5 mm to about 1.5 mm or about 0.75 mm to about 1.25 mm). In at least one example embodiment, the wick 90 includes braided amorphous silica fibers.

A thicker wick 90 may deliver a larger quantity of pre-vapor formulation to the heating element 85' so as to produce a larger amount of vapor, while a thinner wick 90 may deliver a smaller quantity of pre-vapor formulation to the heating element 85' so as to produce a smaller amount of vapor.

In at least one example embodiment, the wick 90 may include a stiff, structural layer and at least one additional less rigid layer. The addition of a stiff, structural layer may aid in automated manufacture of the cartridge. The stiff, structural layer could be formed of a ceramic or other substantially heat resistant material.

Figure 3B:
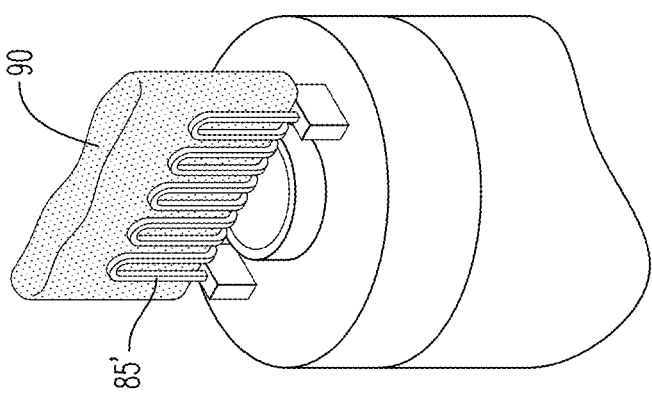
FIG. 3B is a perspective view of a heating element and a wick of the cartridge of FIG. 3A according to at least one example embodiment.

FIG. 3B is a perspective view of a heating element and a wick of the cartridge of FIG. 3A according to at least one example embodiment.

In at least one example embodiment, as shown in FIG. 3B, the heating element 85' may include a folded metal sheet, which at least partially surrounds the wick 90. In at least one example embodiment, the folded heating element 85' is a single integral member that is cut and/or laser etched from a sheet of metal, which is folded about at least a portion of a wick 90. The folded heating element 85' contacts the wick 90 on three sides.

In at least one example embodiment, the folded heating element 85' includes a first plurality of U-shaped segments arranged in a first direction and defining a first side of the heating element 85'. The folded heating element 85' also includes a second plurality of U-shaped segments arranged in the first direction and defining a second side of the heating element 85'. The second side is substantially parallel to the first side.

In at least one example embodiment, the folded heating element 85' also includes ends, which form a first lead portion and a second lead portion.

Figure 4:
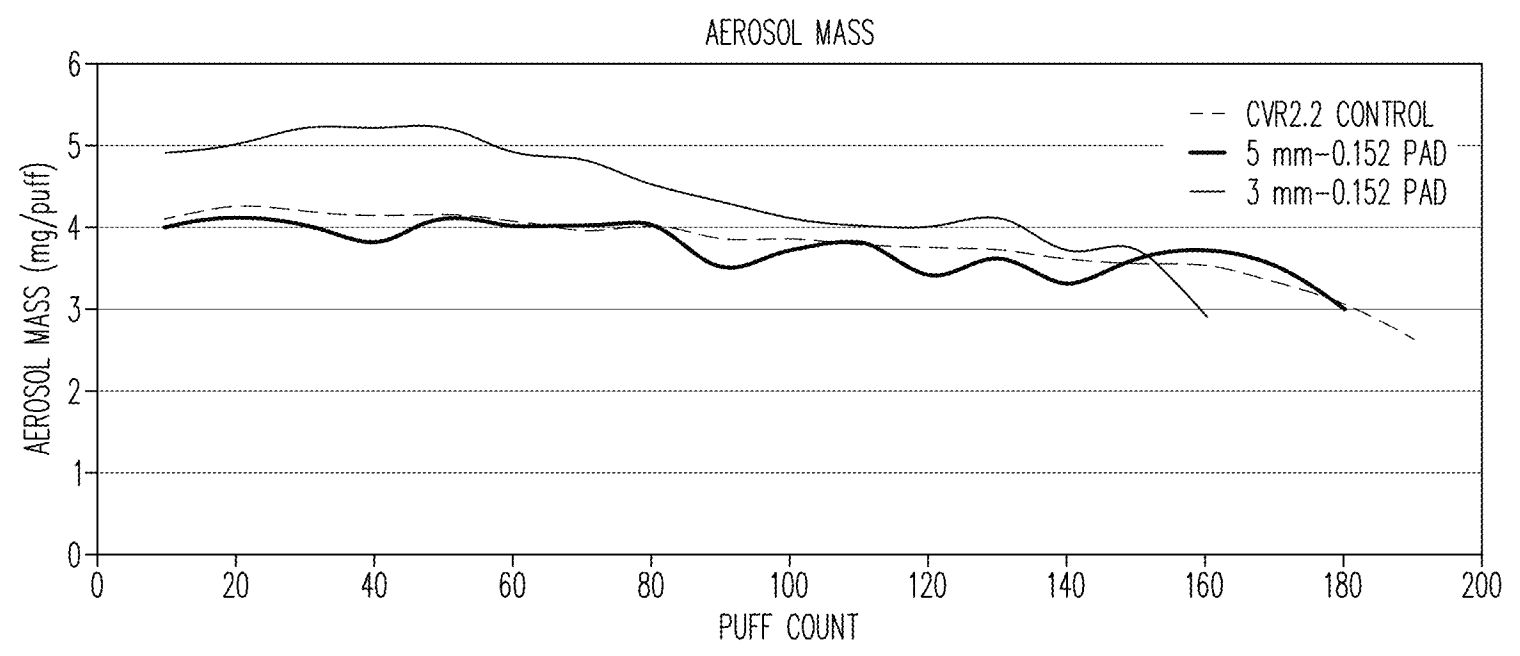

FIG. 4 is a graph comparing electronic vaping devices including transfer pads having different densities and/or lengths according to at least one example embodiment.

Aerosol mass of three different electronic vaping devices were compared. The first electronic vaping device (the first device) was a MARK TEN® electronic vaping device with about 0.9 g of pre-vapor formulation. The second electronic vaping device (the second device) included a cartridge having the configuration as set forth FIGS. 3A and 3B, and included an inner tube having a 1.6 mm inner diameter and the transfer pad 200 as described herein. The transfer pad had a length of about 5 mm and a density of about 0.152 g/cc. The third electronic vaping device (the third device) included a cartridge having the configuration as set forth FIGS. 3A and 3B, and included the transfer pad 200 as described herein. The transfer pad of the third electronic vaping device had a length of about 3 mm and a density of about 0.152 g/cc. The heater of each of the three devices had a resistance of about 3.5 ohms. The resistance-to-draw (RTD) of the first device was about 103 mm $H_2O$, the RTD of the second device was about 128 mm $H_2O$, and the RTD of the third device was about 129 mm $H_2O$.

To determine the aerosol mass, the machine smoking parameters are verified. The puff profile, puff volume, puff duration, puff time, puff frequency and number of puffs are all checked for accuracy before testing. Typical settings are: Square wave puff profile [08], puff volume 55.0 ml [64]%, puff duration 5 seconds [50], puff time 4.9 seconds [49], puff frequency 25 seconds [10], and number of puffs preset [10].

As shown in FIG. 3, the third vaping device provides a larger aerosol mass over time than the second device including the transfer pad having a longer length. Thus, delivery of the pre-vapor formulation is improved in a vaping device in which the transfer pad is shorter. Moreover, the aerosol mass of the third device was greater than the aerosol mass of the first device for about 150 puffs.

Figure 5:
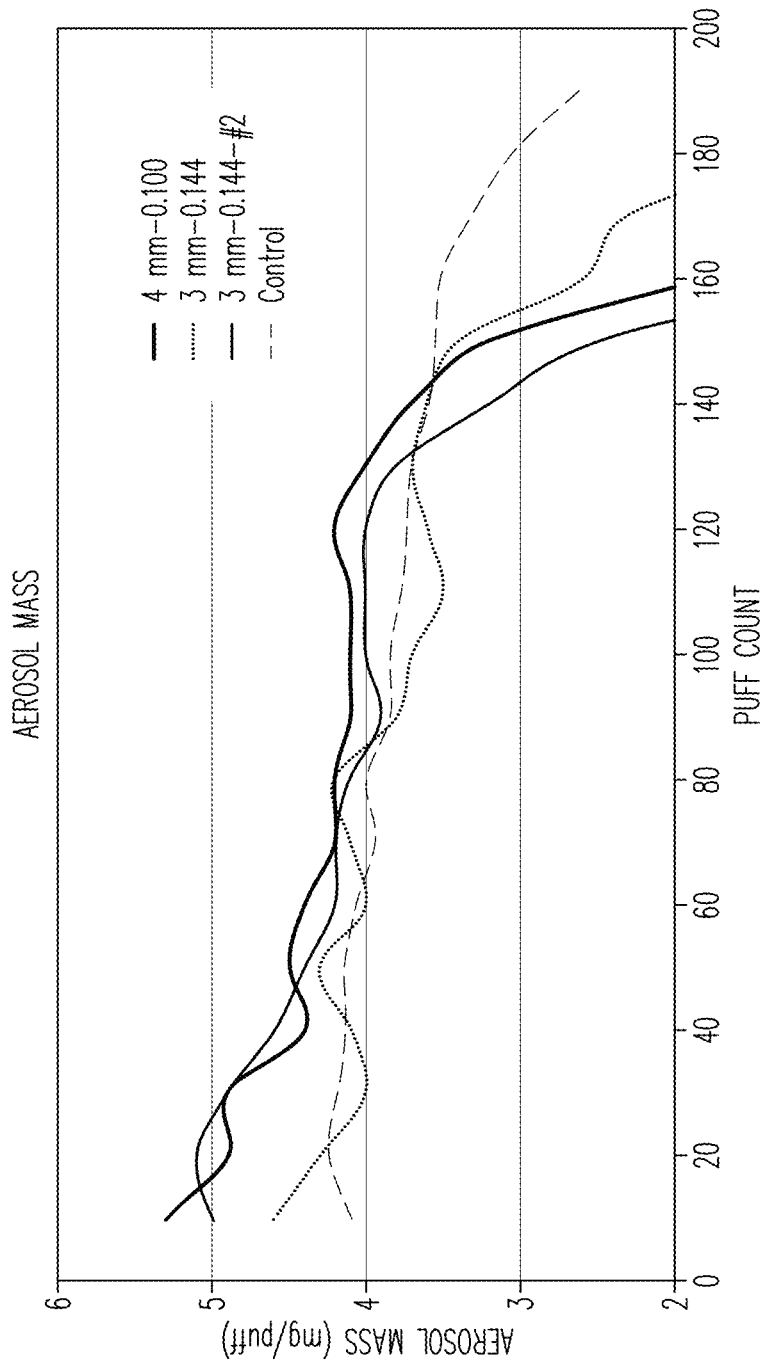
FIG. 5 is a graph comparing electronic vaping devices including transfer pads having different densities and/or lengths according to at least one example embodiment.

FIG. 5 is a graph comparing electronic vaping devices including transfer pads having different densities and/or lengths according to at least one example embodiment.

Aerosol mass of four different electronic vaping devices were compared. The electronic vaping device A (device A) was a MARK TEN® electronic vaping device with about 0.9 g of pre-vapor formulation, which was the control device. The electronic vaping device B (device B) included a cartridge having the configuration as set forth FIGS. 3A and 3B, but included an inner tube having a 1.6 mm inner diameter and the transfer pad 200 as described herein. The transfer pad of device B had a length of about 4 mm and a density of about 0.100 g/cc. The electronic vaping device C (device C) included a cartridge having the configuration as set forth FIGS. 3A and 3B, but included the transfer pad 200 as described herein. The transfer pad of device C had a length of about 3 mm and a density of about 0.144 g/cc. The electronic vaping device D (device D) included a cartridge having the configuration as set forth FIGS. 3A and 3B, but included the transfer pad 200 as described herein. The transfer pad of device D had a length of about 3 mm and a density of about 0.144 g/cc. The heater of each of the three devices had a resistance of about 3.5 ohms.

The aerosol mass of each device is tested as set forth above.

As shown in FIG. 5, device B performs similarly to device D having a shorter length and higher density. Moreover, both device B and device D provide a greater aerosol mass over 140 puffs than the control device.

Accordingly, while not wishing to be bound by theory, it is believed that including a transfer pad having a shorter length and a higher density may perform similarly to an electronic vaping device including a transfer pad having a longer length and a lower density.

Figure 6:
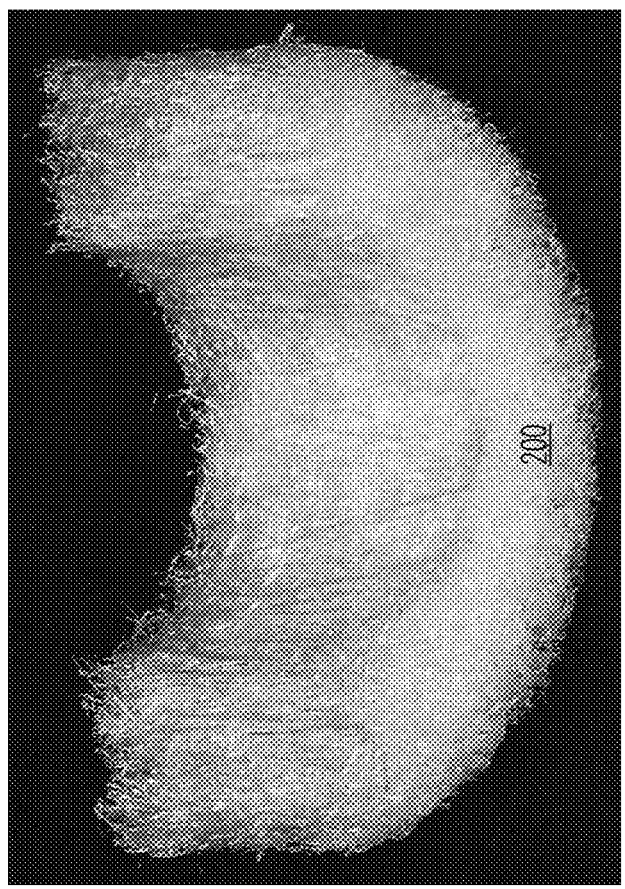
FIG. 6 is a photograph of cross-section of a transfer pad according to at least one example embodiment.

FIG. 6 is a photograph of cross-section of a transfer pad according to at least one example embodiment.

In at least one example embodiment, as shown in FIG. 6, the transfer pad 200 includes the plurality of fibers. When viewing the transfer pad 200, it the plurality of fibers are substantially parallel.

Figure 7:
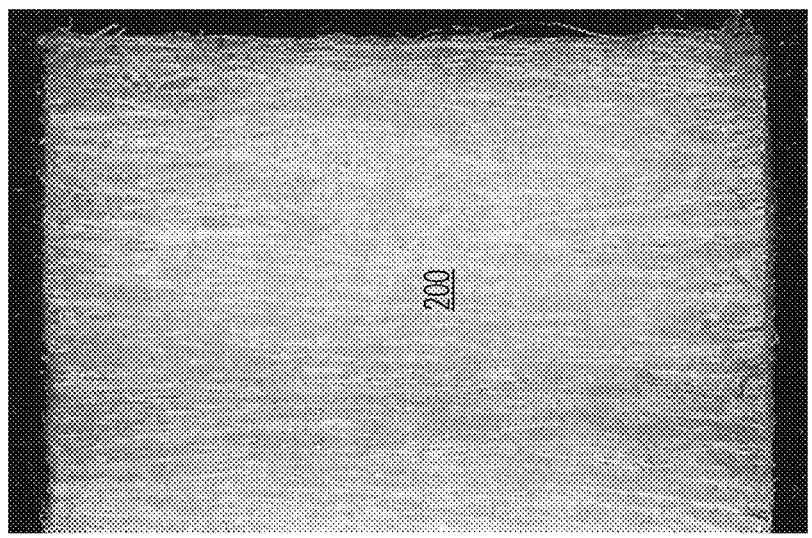
FIG. 7 is an enlarged photograph of a transfer pad according to at least one example embodiment.

FIG. 7 is an enlarged photograph of a transfer pad according to at least one example embodiment.

In at least one example embodiment, as shown in FIG. 7, the transfer pad 200 includes the plurality of fibers. When viewing an enlarged view of the transfer pad 200, it is shown that the plurality of fibers are substantially parallel so as to form channels between adjacent ones of the plurality of fibers.

Figure 8:
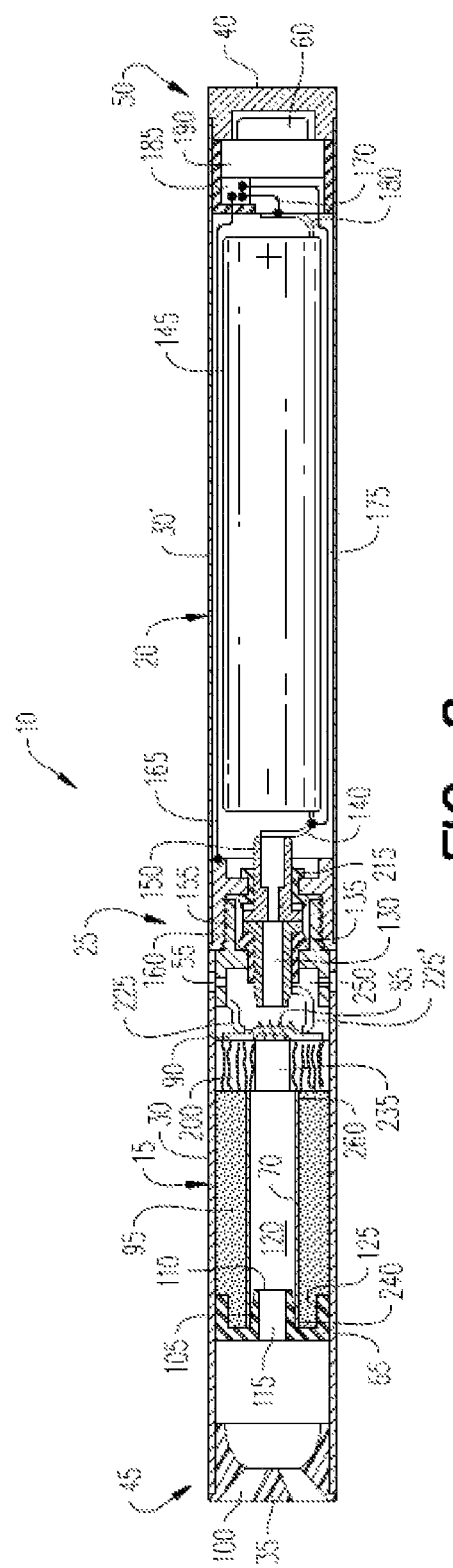
FIG. 8 is a side view of an electronic vaping device according to at least on example embodiment.

FIG. 8 is a side view of an electronic vaping device according to at least on example embodiment.

In at least one example embodiment, as shown in FIG. 8, the electronic vaping device is the same as in FIG. 2 except that the heating element 85 is a heating coil that surrounds a portion of the wick 90.

Figure 9:
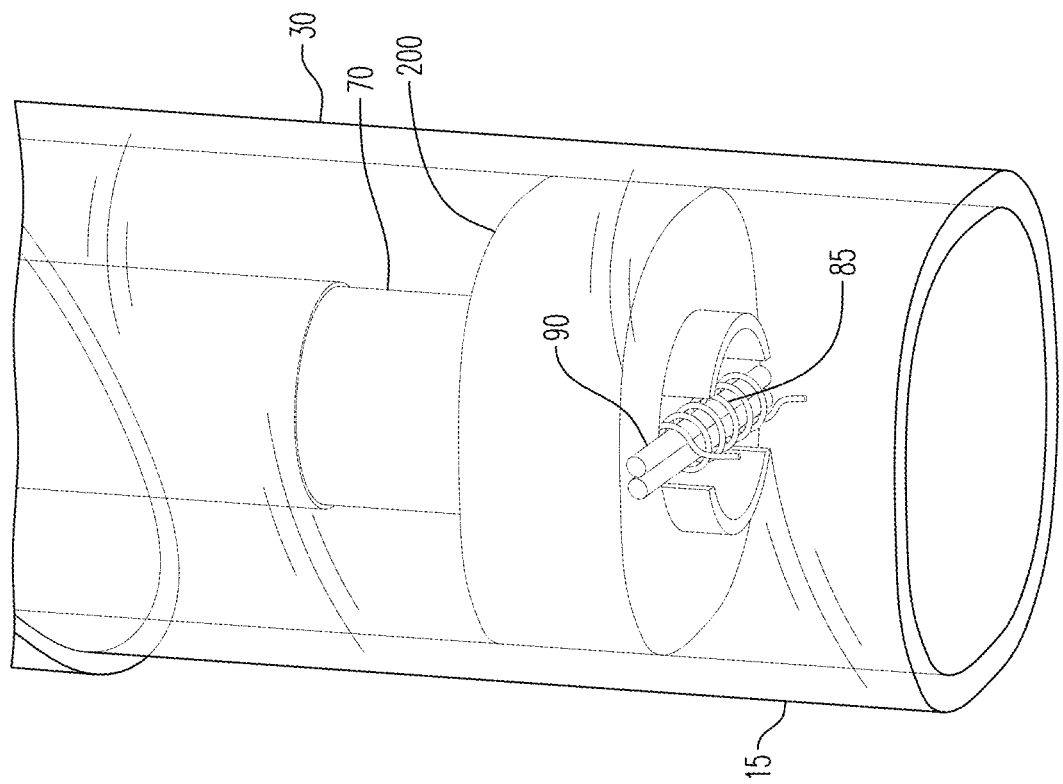
FIG. 9 is a perspective view of a transfer pad in a cartridge, a housing the cartridge being transparent, according to at least one example embodiment.

FIG. 9 is a perspective view of a transfer pad in a cartridge, a housing of the cartridge being transparent, according to at least one example embodiment.

In at least one example embodiment, as shown in FIG. 9, the cartridge 15 is the same as in FIG. 8, except that the housing 30 of the cartridge 15 and the transfer pad 200 each have a generally square-shaped cross-section with generally rounded corners ("squircle"). The transfer pad 200 is about 3.0 mm in length so as to substantially prevent and/or reduce a weight of the transfer pad 200 from becoming too heavy when the transfer pad 200 becomes saturated with the pre-vapor formulation, and to substantially avoid and/or reduce movement of the transfer pad 200 within the cartridge 15 resulting from the weight thereof.

Figure 10:
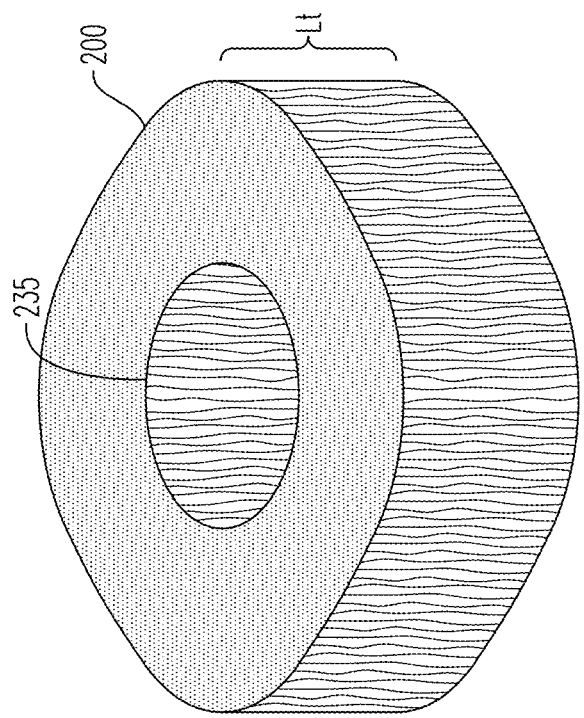
FIG. 10 is a perspective view of the transfer pad of FIG. 9 according to at least one example embodiment.

FIG. 10 is a perspective view of the transfer pad of FIG. 9 according to at least one example embodiment.

In at least one example embodiment, as shown in FIG. 10, the transfer pad 200 is the same as in FIG. 89, but it shown as having a length Lt of about 3.0 mm. The transfer pad 200 defines the air passage 235 therethrough. As shown, the air passage 235 has a generally circular cross-section and the cross-section of an outer surface of transfer pad 200 is different than a cross-section of the air passage 235.

In other example embodiments, not shown, the housing 30 and the transfer pad 200 may have other cross-sectional shapes, including triangular, rectangular, oval, or any other suitable shape.

To test the cartridges for leaks, the following procedure was followed to determine to (time before incubation), $t_{end}$ (time after incubation), $\Delta$weight (mg)=$wt_{0(mg)}$-$wt_{end(mg)}$, and $\Delta$weight (%)=(($wt_{0(mg)}$-$t_{end(mg)}$)/fill weight)*100. The test utilized a vacuum oven (VO-200 Memmert or equivalent with a vacuum pump) and an analytical balance (OHAUS PA214C or equivalent).

To determine leakage, empty cartridges are weighed together with the parts used for assembly if needed (e.g. mouthpiece, sealing ring). Each cartridge is filled with a pre-vapor formulation. The full Cartridges are assembled if needed (e.g. mouthpiece, sealing ring) and weighed. The full Cartridges stand for about 30 minutes at least prior to analysis. The full cartridges are then sealed inside foil bag and inserted into the Vacuum Oven: Ambient/500 mbar. The cartridges are incubated for about 24 hours. Then the foil bag is opened and visually inspected for drops. Each cartridge is then wiped down and weighed. Each cartridge is then puffed 50 puffs (5 second draw/55 ml, 30 sec total). The cartridges are then incubated at about 55° C. overnight in a horizontal position. The cartridges are then wiped and then weighed.

When tested for leakage as set forth above, the cartridge of FIGS. 3A and 3B, including a transfer pad having a density of 0.100 g/cc and no gasket between the liquid reservoir and the heating element and wick showed no leaks. As compared to control cartridge including no transfer pad, but including a seal/gasket between the reservoir and the heating element, the cartridge of FIGS. 3A and 3B performed substantially the same as the control cartridges as shown in Table 1 below.

TABLE 1

| Tank No. | Orientation | Before Oven Weight (g) | After Oven Weight (g) | Weight Difference (g) | Ratio of Weight Change (%) |
| --- | --- | --- | --- | --- | --- |
| 1 | Horizontal | 8.1735 | 8.1741 | 0.0006 | 0.01% |
| 2 | Horizontal | 8.1658 | 8.1671 | 0.0013 | 0.02% |
| 3 | Horizontal | 8.1631 | 8.1639 | 0.0008 | 0.01% |
| C1 | Horizontal | 8.4910 | 8.4932 | 0.0022 | 0.03% |
| C2 | Horizontal | 8.4631 | 8.4645 | 0.0014 | 0.02% |
| C3 | Horizontal | 8.4952 | 8.4968 | 0.0016 | 0.02% |

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A cartridge for an electronic vaping device comprising:
    an outer housing extending in a longitudinal direction;
    a reservoir configured to contain a pre-vapor formulation, the reservoir in the outer housing;
    a transfer pad at an end of the reservoir, the transfer pad including a plurality of fibers, each of the plurality of fibers being substantially parallel to the longitudinal direction;
    a wick in contact with the transfer pad, and
    an inner tube within the outer housing, the reservoir between an outer surface of the inner tube and an inner surface of the outer housing, wherein the transfer pad defines an air channel extending through the transfer pad, and the air channel is sized and configured to fit around the outer surface of the inner tube.

2. The cartridge of claim 1, wherein the reservoir is under atmospheric pressure.

3. The cartridge of claim 1, wherein the transfer pad has a density ranging from about 0.08 g/cc to about 0.3 g/cc.

4. The cartridge of claim 1, wherein the transfer pad has a length of about 5.0 mm to about 10.0 mm and a density of about 0.08 g/cc to about 0.1 g/cc.

5. The cartridge of claim 1, wherein the transfer pad has a length of about 0.5 mm to about 10.0 mm and a density of about 0.1 g/cc to about 0.3 g/cc.

6. The cartridge of claim 1, wherein the transfer pad has a length of about 3.0 mm and the transfer pad has a generally square-shaped cross-section with rounded corners.

7. The cartridge of claim 1, wherein the transfer pad includes an outer side wall, the outer side wall having a coating thereon.

8. The cartridge of claim 1, wherein the plurality of fibers include at least one of polypropylene and polyester.

9. The cartridge of claim 1, further comprising:
    at least one heater in fluid communication with the wick.

10. The cartridge of claim 9, wherein the at least one heater does not contact the transfer pad.

11. The cartridge of claim 1, wherein about 50% to about 100% of the plurality of fibers extend substantially in the longitudinal direction.

12. The cartridge of claim 11, wherein about 75% to about 95% of the plurality of fibers extend substantially in the longitudinal direction.

13. An electronic vaping device comprising:
an outer housing extending in a longitudinal direction;
a reservoir configured to contain a pre-vapor formulation, the reservoir in the outer housing;
a transfer pad at an end of the reservoir, the transfer pad including a plurality of fibers, the plurality of fibers being substantially parallel to the longitudinal direction;
a wick in contact with the transfer pad;
at least one heater in fluid communication with the wick;
a power supply electrically connectable to the at least one heater; and
an inner tube within the outer housing, the reservoir between an outer surface of the inner tube and an inner surface of the outer housing, wherein the transfer pad is between the outer surface of the inner tube and the inner surface of the outer housing, wherein the transfer pad defines an air channel extending through the transfer pad, and the air channel is sized and configured to fit around the outer surface of the inner tube.

14. The electronic vaping device of claim 13, wherein the reservoir is under atmospheric pressure.

15. The electronic vaping device of claim 13, wherein the transfer pad has a density ranging from about 0.08 g/cc to about 0.3 g/cc.

16. The electronic vaping device of claim 13, wherein the transfer pad has a length of about 5.0 mm to about 10.0 mm and a density of about 0.08 g/cc to about 0.1 g/cc.

17. The electronic vaping device of claim 13, wherein the transfer pad has a length of about 0.5 mm to about 5.0 mm and a density of about 0.1 g/cc to about 0.3 g/cc.

18. The electronic vaping device of claim 13, wherein the transfer pad includes an outer side wall, the outer side wall having a coating thereon.

19. The electronic vaping device of claim 13, wherein the transfer pad has a length of about 3.0 mm and the transfer pad has a generally square-shaped cross-section with rounded corners.

20. The electronic vaping device of claim 15, wherein the plurality of fibers include at least one of polypropylene and polyester.

21. The electronic vaping device of claim 15, wherein the at least one heater does not contact the transfer pad.

22. The electronic vaping device of claim 15, wherein about 50% to about 100% of the plurality of fibers extend substantially in the longitudinal direction.

23. The electronic vaping device of claim 22, wherein about 75% to about 95% of the plurality of fibers extend substantially in the longitudinal direction.

* * * * *